US006277980B1

(12) United States Patent
DiPaolo et al.

(10) Patent No.: US 6,277,980 B1
(45) Date of Patent: Aug. 21, 2001

(54) HUMAN PAPILLOMA VIRUS INHIBITION BY ANTI-SENSE OLIGONUCLEOTIDES

(75) Inventors: Joseph DiPaolo; Luis Alvarez-Salas, both of Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/560,579

(22) Filed: Apr. 28, 2000

Related U.S. Application Data

(63) Continuation of application No. 08/929,140, filed on Sep. 5, 1997, now Pat. No. 6,084,090.

(51) Int. Cl.[7] .......................... C07H 21/02; C07H 21/04

(52) U.S. Cl. .................... 536/24.5; 536/23.1; 536/24.1

(58) Field of Search ...................... 536/24.5, 23.1, 536/24.1

(56) References Cited

U.S. PATENT DOCUMENTS 5,683,902  11/1997  Hampel et al. .

FOREIGN PATENT DOCUMENTS

| WO 93/20095 | 10/1993 | (WO) . |
|---|---|---|
| WO 95/13833 | 5/1995 | (WO) . |
| WO 95/31552 | 11/1995 | (WO) . |
| WO9531551 | 11/1995 | (WO) . |
| WO 96/3901 | 12/1996 | (WO) . |

OTHER PUBLICATIONS

Luis M. Alvarez–Salas et al, Inhibition of HPV–16 E6/E7 immortalization of Normal Keratinocytes by Hairpin Ribozymes, Feb. 1998, National Academy of Sciences, vol. 95, pp. 1189–1194.*
Agrawal, et al., Synthesis and Anti–HIV Activity of Oligorbonucleotides and Their Phosphorothioate . . . , Ann. New York Acad. Sci. 660:2–10 (1992).
Agrawal, S., Antisense oligonucleotides: towards clinical trials, TIBTECH 14:3–14 (1996).
Agrawal, et al., Mixed–backbone oligonucleotides as second generation antisense . . . , Proc. Natl. Acad. Sci. USA 94:2620–2625 (1997).
Alvarez–Salas, et al., Transcriptional repression in normal human keratinocytes by wild type . . . , Cancer Lett. 91:85–92 (1995).
Anderson, et al., Mutagenesis of the hairpin ribozyme, Nucl. Acids Res. 22(6):1096–1100 (1994).
Cech, T.R., Ribozymes and Their Medical Implications, JAMA 260(20):3030–3034 (1988).
Chen, et al., Synthesis of oligodeoxyribonucleotide N3–P5 phosphoramidates, Nucl. Acids Res. 23(14):2661–2668 (1995).

Cohen, J.S., Informational Drugs: A New Concept in Pharmacology, Antisense Res. Dev. 1:191–193 (1991).
Dagle, et al., Physical properties of oligonucleotides containing phosphoramidate–modified . . . , Nucl. Acids Res. 19(8):1805–1810 (1991).
DiPaolo, et al., Cellular and Molecular Alterations in Human Epithelial Cells Transformed . . . , Crit. Rev. Oncogen. 4(4):337–360.
EsCude, et al., Stable triple helices formed by oligonucleotide N3–P5 phosphoramidates . . . , Proc. Natl. Acad. Sci. USA 93(9)4365–4369 (1996).
Froehler, et al., Phosphoramidate analogues of DNA: synthesis and thermal stability of heteroduplexes . . . , Nucl. Acids Res. 16(11):4831–4839 (1988).
Gryaznov, et al., Oligonucleotide N3–P5 phosphoramidates as antisense agents, Nucl. Acids Res. 24(8):1508–1514 (1996).
Hamada, et al., Adenovirus–Mediated Transfer of HPV 16 E6/E7 Antisense RNA to Human Cervical Cancer Cells, Gynecol. Oncol. 63:219–227 (1996).
Hampel, et al., RNA Catalytic Properties of the Minimum (–)sTRSV Sequence, Biochem. 28:4929–4933 (1989).
Hampel, et al., "Hairpin" catalytic RNA model: evidence for helices and sequence requirement for . . . , Nucl. Acids Res. 18(2):299–304 (1990).
Haseloff, et al., Sequence required for self–catalysed cleavage of the satellite RNA of tobacco . . . , Gene 82:43–52 (1989).
Hawley–Nelson, et al., HPV16 E6 and E7 proteins cooperate to immortalize human foreskin keratinocytes, EMBO J. 8(12):3905–3910 (1989).
Henry, et al., Comparison of the toxicity profiles of ISIS 1082 and ISIS 2105, phosphorothioate . . . , Toxicol. 116:77–88 (1997).
Henry, et al., Toxicological properties of several novel oligonucleotide analogs in mice, Anticancer Drug Des. 12:1–14 (1997).
Kean, et al., Inhibition of Herpes simplex virus Replication by Antisense Oligo–2–0–methylribonucleoside . . . , Biochem. 34(45):14617–14620 (1995).
Marshall, et al., Inhibition of human immunodeficiency virus activity by phosphorodithioate . . . , Proc. Natl. Sci. USA 89:6265–6269.

(List continued on next page.)

Primary Examiner—Sean McGarry
(74) Attorney, Agent, or Firm—Knobbe, Martens, Olson & Bear, LLP

(57) ABSTRACT

Antisense oligonucleotides having phosphorothioate backbone structure and sequences complementary to nucleotides contained with residues 415 to 445 of human papilloma virus 16 (HPV-16) are disclosed. Methods of treatment using antisense oligonucleotides having phosphorothioate backbone structure and nucleotide sequences complementary to nucleotides contained with residues 415 to 445 of HPV-16 are disclosed.

1 Claim, 7 Drawing Sheets

OTHER PUBLICATIONS

McKay, et al., Enhanced activity of an antisense oligonucleotide targeting murine protein kinase . . . , Nucl. Acids Res. 24(3):411–417 (1996).

Metelev, et al., Study of Antisense Oligonucleotide Phosphorothioates Containing Segments . . . , Bioorg. Med. Chem. Lett. 4(24):2929–2934 1994.

Miller, et al., Anticode Oligonucleoside Methylphosphonates and Their Psoralen Derivatives, Antisense Res. and Appl. pp. 189–203 (1993).

Monia, et al., Antitumor activity of a phosphorothioate antisense oligodeoxynucleotide . . . , Nature Medicine 2(6):668–675 (1996).

Monia, et al., Evaluation of 2–Modified Oligonucleotides Containing 2–Deoxy Gaps . . . , J. Biol. Chem. 268(19):14514–14522 (1993).

Ojwang, et al., Inhibition of human immunodeficiency virus type 1 expression by . . . , Proc. Natl. Acad. Sci. USA 89:10802–10806 (1992).

Phelps, et al., The Human Papillomavirus Type 16 E7 Gene Encodes Transactivation . . . , Cell 53:539–547 (1988).

Pirisi et al., Continuous cell lines with altered growth and differentiation . . . , Carcinogen. 9(9):1573–1579 (1988).

Roush, W., Antisense Aims for a Renaissance, Science 276:1192–1193.

Sarin, et al., Inhibition of acquired immunodeficiency syndrome virus by oligodeoxynucleoside . . . , Proc. Natl. Acad. Sci. USA 85:7448–7451 (1988).

Scheffner, et al., The E6 Oncoprotein Encoded by Human Papillomavirus Types 16 and 18 . . . , Cell 63:1129–1136 (1990).

Schiffman, et al., New Epidemiology of Human Papillomavirus Infection and Cervical Neoplasia, J. Natl. Cancer Inst. 87(18):1345–1347 (1995).

Skorski, et al., Antileukemia efect of c–myc N3–P5 phosphoramidate antisense . . . , Proc. Natl. Acad. Sci. USA 94:3966–3971 (1997).

Steele, et al., Effects of Human Papillomavirus Type 18–specific Antisense Oligonucleotides on the Transformed . . . , Cancer Res. 53–2330–2337 (1993).

Storey, et al., Anti–sense phosphorothioate oligonucleotides have both specific and non–specific . . . , Nucl. Acids Res. 19(15):6209–6224 (1987).

Tanaka, et al., Synthesis of oligodeoxyribonucleotide with aliphatic amino or phosphate group at the 5 . . . , Nucl. Acids Res. 19(15):6209–6224 (1987).

Viallet, et al., Characterization of Human Bronchial Epithelial Cells Immortalized by the . . . , Exp. Cell Res. 212:36–41 (1994).

von Knebel Doeberitz, et al. Analysis of the Biological Role of Human Papilloma Virus (HPV) . . . , Hamatol. Bluttransfus. 31:377–279 (1987).

Walder, J., Antisense DNA and RNA: progress and prospects, Genes Dev. 2:502–504 (1988).

Yokoyama, et al., Human Papillomavirus 18–Immortalized Endocervical Cells With In Vitro Cytokeratin . . . , Obstet. Gynecol. 83(2):197–204 (1994).

Yu, et al., A hairpin ribozyme inhibits expression of diverse strains of human immunodeficiency . . . , Proc. Natl. Acad. Sci. USA 90:6340–6344 (1993).

Zerfass, et al., Sequential Activation of Cyclic E and Cyclin A Gene Expression by Human . . . , J. Virol. 69(10):6389–6399 (1995).

zur Hausen, et al., Human Papillomaviruses, Annu. Rev. Microbiol. 48:427–447 (1994).

Stull et al., Antigene, Ribozyme and aptamer nucleic acid drugs: Progress & Prospects, Pharmaceutical Research 12(4):465–483 (1995).

Uwlman et al., Antisense Oligonucleotides: A New Therapeutic Principle, Chemical Reviews 90(4):543–584 (1990).

* cited by examiner

HUMAN PAPILLOMA VIRUS INHIBITION BY ANTI-SENSE OLIGONUCLEOTIDES

RELATED APPLICATIONS

This application is a continuation of allowed U.S. application Ser. No. 08/929,140, filed Sep. 5, 1997 and now U.S. Pat. No. 6,084,090, the entire contents of which are incorporated herein by reference.

Subject matter related to the present application is disclosed in allowed U.S. Ser. No. 08/410,005, filed Mar. 21, 1995 and now U.S. Pat. No. 5,683,902, which is a continuation of U.S. Ser. No. 08/242,665, filed May 13, 1994, now abandoned, which is hereby incorporated by reference. Also hereby incorporated by reference is U.S. Ser. No. 08/737,454, now abandoned, which corresponds to International Patent Application PCT/US95/06016, filed May 15, 1995, which claims priority to U.S. Ser. No. 08/242,665.

FIELD OF THE INVENTION

The present invention relates to the use of antisense oligonucleotides to inhibit a Human Papilloma virus (HPV), and specifically relates to use of antisense oligonucleotides specific for nucleotides 415 to 445 of the DNA sequence of HPV-16.

BACKGROUND OF THE INVENTION

Papilloma viruses are small DNA viruses that induce the hyper proliferation of epithelial cells. Approximately 70 different genotypes of human papilloma virus (HPV) have been isolated. Some HPV genotypes (e.g., 1, 2, 4, and 7) have been associated with human benign squamous papillomas (warts and condylomas) and others (e.g., 16 and 18) have been associated with human neoplastic and preneoplastic lesions (DiPaolo, et al., 1993, Crit. Rev. Oncogen. 4:337–360).

HPV-16 has been associated with a variety of clinical conditions in both women and men. In women, HPV-16 is frequently associated with latent infections, benign and premalignant cervical lesions (dysplasias/CIN) and half of invasive cervical carcinomas. Cervical cancer, which kills at least 500,000 women worldwide each year, proceeds through progressive cellular changes from benign condylomata to high-grade dysplasias/CIN before developing into an invasive cancer. In men, HPV-16 is associated with subclinical macular or clinical papular lesions. Penile Bowenoid papulosis which resembles carcinoma in situ. Detection and treatment of these lesions costs over five billion health care dollars annually in the United States.

HPV-16 has been associated with over half of invasive cervical carcinomas worldwide and with many cell lines derived from cervical carcinomas. HPV-16 expression causes benign proliferation and efficiently immortalizes cultured human epithelial cells, including cervical keratinocytes (DiPaolo, et al., 1993, Crit. Rev. Oncogen. 4:337–360; Zur Hausen & de Villiers, 1994, Annu. Rev. Microbiol. 48:427–447; Schiffman, 1995, J Natl. Cancer Inst. 87:1345–1347). Two HPV-16 genes, E6 and E7, and their gene products are required to immortalize a human keratinocytes and are a hallmark of cervical carcinoma (Hawley-Nelson et al., 1989, EMBO J. 8:3905–3910; Phelps et al., 1988, Cell 53:539–547; Viallet et al., 1994, Exp. Cell Res. 212:36–41; Yokoyama et al., Obstet. Gynecol. 83:197–204). The E6 and E7 proteins bind to other gene products (p53 and Rb tumor suppressors) to disrupt control of cell division and proliferation, leading to transformation (Scheffner et al., 1990, Cell 63:1129–1136; Zerfass et al., J. Virol 69:6389–6399).

Surgery is commonly used for treatment of high-grade lesions due to the lack of effective alternatives. Cervical laser ablation therapy, however, does not in the long term influence the natural history of cervical human papillomavirus-associated diseases in women. Interferons have not proved an effective antiviral or anticancer treatment. Chemotherapy (e.g., cisplatin, alone or combined with other chemotherapy agents such as 5FU) has generally not proved to be effective in treatment of many cervical cancers. Moreover, most chemotherapeutic agents are cytotoxic, leading to toxic side effects and the development of multiple drug resistance. Therefore, there is a need for reagents than can specifically inhibit the growth of HPV-associated tumor cells, while avoiding serious toxic reactions.

HPV-specific treatments in the form of cleavage of HPV-specific RNA with ribozymes and inhibition by HPV-specific antisense oligonucleotides have been suggested (PCT International Patent Application WO 95/31552; DiPaolo, et al., 1993, Crit. Rev. Oncogen.4:337–360; Steele, et al., 1993, Cancer Res. 53:2330; Storey, et al., 1991, Nuc. Acids Res. 19(15):4109). Ribozymes are small catalytic RNA molecules that can hybridize to and cleave a complementary RNA target (Cech, 1988, JAMA 260:3030–3034). Ribozymes having a "hairpin" motif have been found to be more efficient than the "hammerhead" motif (Hampel & Tritz, 1989, Biochem. 28:4929–4933; Hampel, et al., 1990, Nuc. Acids Res. 18:299–304) and "hairpin" ribozymes have been used to cleave viral targets, including the human immunodeficiency virus (HIV-1) and HPV (Ojwang, et al., 1992, Proc. Natl. Acad. Sci. USA 89, 10802–10806; Yu, et al., 1993, Proc. Natl. Acad. Sci. USA 90:6340–6344; PCT International Patent Application WO 95/31552).

Antisense RNA and oligonucleotides hybridize to complementary mRNA, thus blocking translation and promoting the activity of endogenous RNase H to cleave the mRNA (Walder, 1988, Genes Dev. 2:502–504; Cohen, 1991, Antisense Res. Dev. 1:191–193). Although antisense RNA and oligonucleotides should be specific for their target sequence, nonspecific toxicity has been observed (Henry et al., 1997, Toxicol. 116:77–88; Henry et al., 1997, Anticancer Drug Des. 12:1–14). First-generation antisense phosphorothioates, whose nucleotide backbones carry sulfur atoms to slow intracellular degradation were often ineffective because of inability to enter cells or to complement the target mRNA, but improved second generation phosphorothioate antisense therapies, referred to as "mixed backbone oligonucleotides" and "end-modified chimerics" that carry 2'-O-methylribonucleoside moieties have proven effective in clinical trials (Monia et al., 1996, Nature Medicine 6:668–675; Roush, 1997, Science 276:1192–1193; Agrawal et al., 1997, Proc. Natl. Acad. Sci. USA 94:2620–2625; Agrawal, 1996, TIBTECH 14:3–14).

Antisense inhibition of HPV-18 E6 and E7 expression in cell lines (C4-1 and HeLa) resulted in a significant decrease in growth rate with continuous addition of oligonucleotide (Steele, et al., 1993, Cancer Res. 53:2330–2337). Similar results have been observed in cells transfected with recombinant vectors (von Knebel Doeberitz & Grissmann, 1987, Hamatol. Bluttransfus. 31:377–279; Hamada et al., 1996, Gynecol. Oncol. 63:219–227).

The present invention discloses oligonucleotide sequences and methods of antisense therapy using antisense oligonucleotides defined by selected HPV-16 complementary sequences.

SUMMARY OF THE INVENTION

According to the present invention, antisense oligonucleotides that specifically bind to a human papilloma virus-16 (HPV-16) sequence include sequences complementary to viral sequences between viral nucleotide 415 and 445.

One aspect of the present invention relates to analogs of antisense oligonucleotides comprising oligonucleotide sequences complementary to SEQ ID NO:2 or SEQ ID NO:3, wherein the analogs are phosphorothioate antisense oligonucleotides in which at least one phosphodiester bond is replaced with a phosphorothioate bond, mixed backbone antisense oligonucleotides in which at least one phosphodiester bond is replaced with a phosphorothioate bond and at least one phosphodiester bond is replaced with a 2'-O-methylnucleoside phophodiester bond, end-modified analogs in which at least one end has a 2'-O-methylnucleotide moiety, methylphosphonates, phosphoramidates, phosphorodithioates, or N3'→P5'-phosphoramidates.

Another aspect of the present invention relates to analogs of antisense oligonucleotides comprising sequences of SEQ ID NO:6, SEQ ID NO:7 or SEQ ID NO:17, wherein the analogs are phosphorothioate oligonucleotides in which at least one phosphodiester bond is replaced with a phosphorothioate bond, mixed backbone oligonucleotides in which at least one phosphodiester bond is replaced with a phosphorothioate bond and at least one phosphodiester bond is replaced with a 2'-O-methylnucleoside phophodiester bond, end-modified oligonucleotides in which at least one end has a 2'-O-methylnucleotide moiety, methylphosphonates, phosphoramidates, phosphorodithioates, or N3'→P5'-phosphoramidates.

Another aspect relates to analogs of antisense oligoribonucleotides of SEQ ID NO:4, SEQ ID NO:5 or SEQ ID NO:16, wherein the analogs are oligoribonucleotide phosphorothioates, 2'-O-alkyl oligoribonucleotide phosphorothioates or 2'-O-methylribonucleotide methylphosphonates. Yet another aspect of the invention relates to an antisense therapeutic composition comprising an oligonucleotide sequence of SEQ ID NO:9 and a pharmaceutically acceptable carrier.

Therapeutic compositions include any of the foregoing analogs and a pharmaceutically acceptable carrier. The therapeutic compositions can also include a ribozyme containing sequences complementary to SEQ ID NO:2 or SEQ ID NO:3.

Yet one more aspect of the present invention relates to a method of preventing transformation of a living cell by HPV. The method includes providing an antisense therapeutic composition as is described above, providing a living cell capable of being transformed by HPV, transfecting the living cell with the antisense therapeutic composition; and maintaining the living cell alive for sufficient time to inhibit expression of HPV gene E6.

Still another aspect of the present invention is also a method of preventing transformation of a living cell by HPV. This method includes providing antisense oligonucleotides having sequences complementary to SEQ ID NO:2 or SEQ ID NO:3, providing a living cell capable of being transformed by HPV, transfecting the antisense oligonucleotides into the living cell, and maintaining the living cell alive for sufficient time to inhibit expression of HPV gene E6. The living cell can be a human keratinocyte, a human cervical cell, or other living cell.

An additional aspect of the invention relates to a method of inhibiting expression of HPV gene E6 in a living cell. This method includes the steps of: providing antisense oligonucleotides having sequences of SEQ ID NO:6, SEQ ID NO:7 or SEQ ID NO:17, providing a biological sample comprising living cells capable of being infected with HPV; transfecting the antisense oligonucleotides into the living cells; and maintaining the living cells alive for sufficient time to allow inhibition of HPV E6 gene expression to occur. The method can also include repeating the transfecting and maintaining steps. The living cell can be a human keratinocyte, a human cervical cell, or other living cell. The step of providing antisense oligonucleotides can include administering antisense oligonucleotides to a living organism by s.c., i.p. or i.v. injection or by painting the antisense oligonucleotides onto the biological sample in situ.

Another aspect of the invention is also a method of inhibiting expression of HPV gene E6 in a living cell. This method includes the steps of: providing antisense oligonucleotide analogs having sequences of SEQ ID NO:6, SEQ ID NO:7 or SEQ ID NO:17, wherein the antisense oligonucleotide analogs are phosphorothioate oligonucleotides in which at least one phosphodiester bond is replaced with a phosphorothioate bond, mixed backbone oligonucleotides in which at least one phosphodiester bond is replaced with a phosphorothioate bond and at least one phosphodiester bond is replaced with a 2'-O-methylnucleoside phophodiester bond, in which at least one end has a 2'-O-methylnucleotide moiety, rrethylphosphonates, phosphoramidates, phosphorodithioates, or N3'→P5'-phosphoramidates, providing a biological sample comprising living cells capable of being infected with HPV; transfecting the antisense oligonucleotide analogs into the living cells; and maintaining the living cells alive for sufficient time to allow inhibition of HPV E6 gene expression to occur.

The present invention also includes another aspect which is a method of inhibiting expression of HPV gene E6 in a living call. This method includes the steps of: providing antisense oligoribonucleotide analogs of oligoribonucleotides of SEQ ID NO:4, SEQ ID NO:5 or SEQ ID NO:16, wherein the analogs are oligoribonucleotide phosphorothioates, 2'-O-alkyl oligoribonucleotide phosphorothioates or 2'-O-methylribonucleotide methylphosphonates, providing a biological sample comprising living cells capable of being infected with HPV, transfecting the antisense oligoribonucleotide analogs into the living cells, and maintaining the living cells alive for sufficient time to allow inhibition of HPV E6 gene expression to occur.

DETAILED DESCRIPTION OF THE PREFERRED EMBODIMENT

Figure 1:
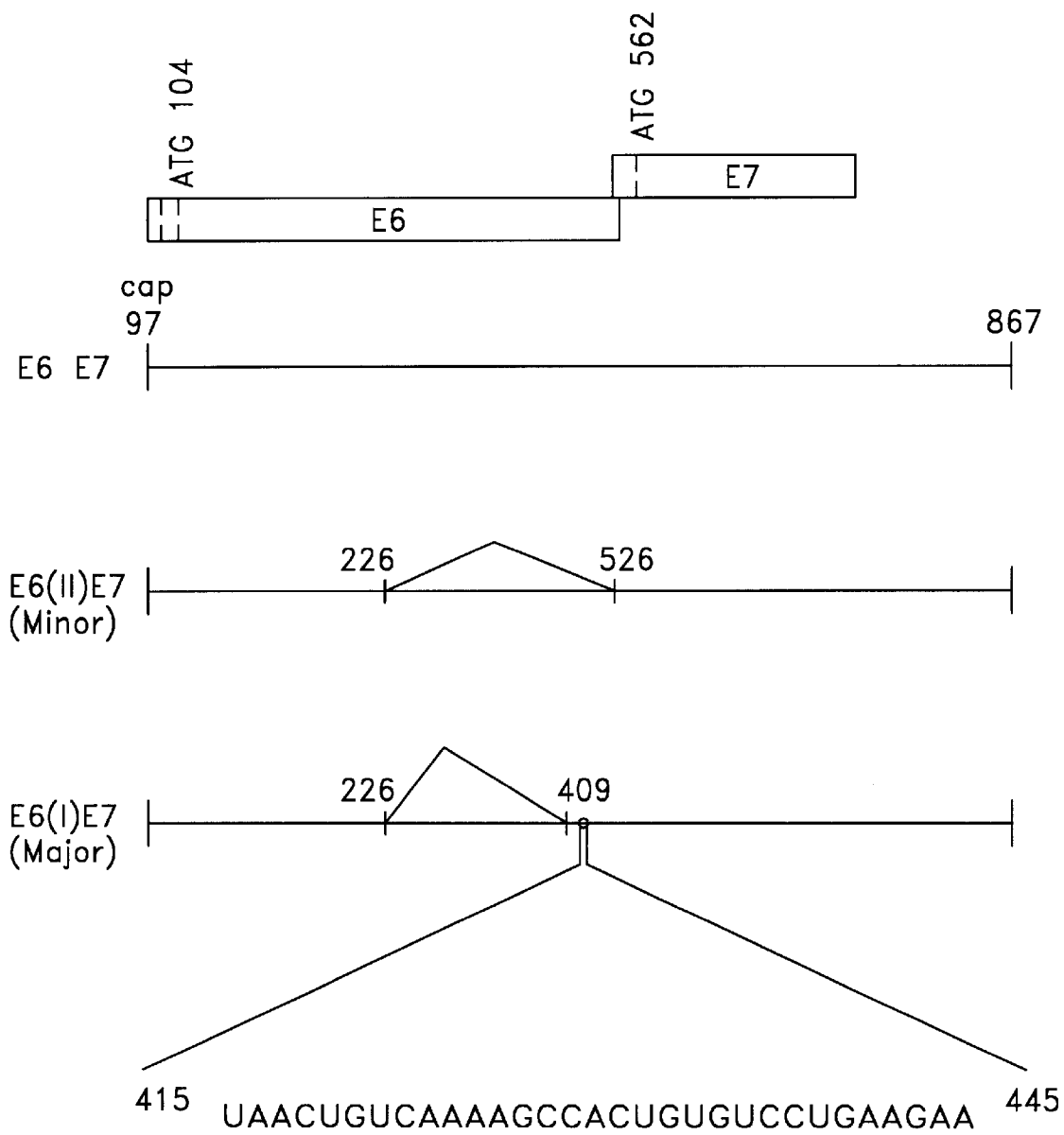
FIG. 1 is a diagram of the HPV-16 E6/E7 target sites showing the overlaps in the E6/E7 mRNA and the ATG sites of E6 (at nt 104) and of E7 (at nt 562), the primary mRNA transcript having a cap at nt 97 and terminating at nt 867, a minor form of processed E6/E7 mRNA ("E6(II)E7") spliced at nt 226 and 526, and a major form of processed E6/E7 mRNA ("E6(I)E7") spliced at nt 226 and 409, and the relative position of the antisense target sequence between nt 415 and 445. The complete HPV-16 sequence (GenBank Accession No. K02718) is presented in SEQ ID NO:1 and the antisense target sequence between nt 415–445 occurs therein.

Because the E6 and E7 genes overlap and produce mRNA molecules that overlap the two genes (as shown in FIG. 1), the E6 and E7 genes together and their mRNA overlapping transcripts will be generally referred to herein as E6/E7 genes and E6/E7 mRNA, respectively.

In the course of characterizing ribozymes that cleave E6/E7 mRNA, ribozymes that are inactive because of changes to the hairpin structure of the ribozyme were found to inhibit cell proliferation in vitro showing that the ribozymes were, in fact, acting at least in part as antisense inhibitors. That is, even in the absence of ribozyme-mediated cleavage of E6/E7 mRNA, the introduced ribozyme sequences that contain antisense sequences directed to E6/E7 target sequences were capable of limiting the amount of full-length E6/E7 transcripts. These antisense sequences are the basis for antisense oligonucleotides having modified backbone structure for use as antisense therapeutics.

Ribozyme Constructs and Activity

Figure 2:
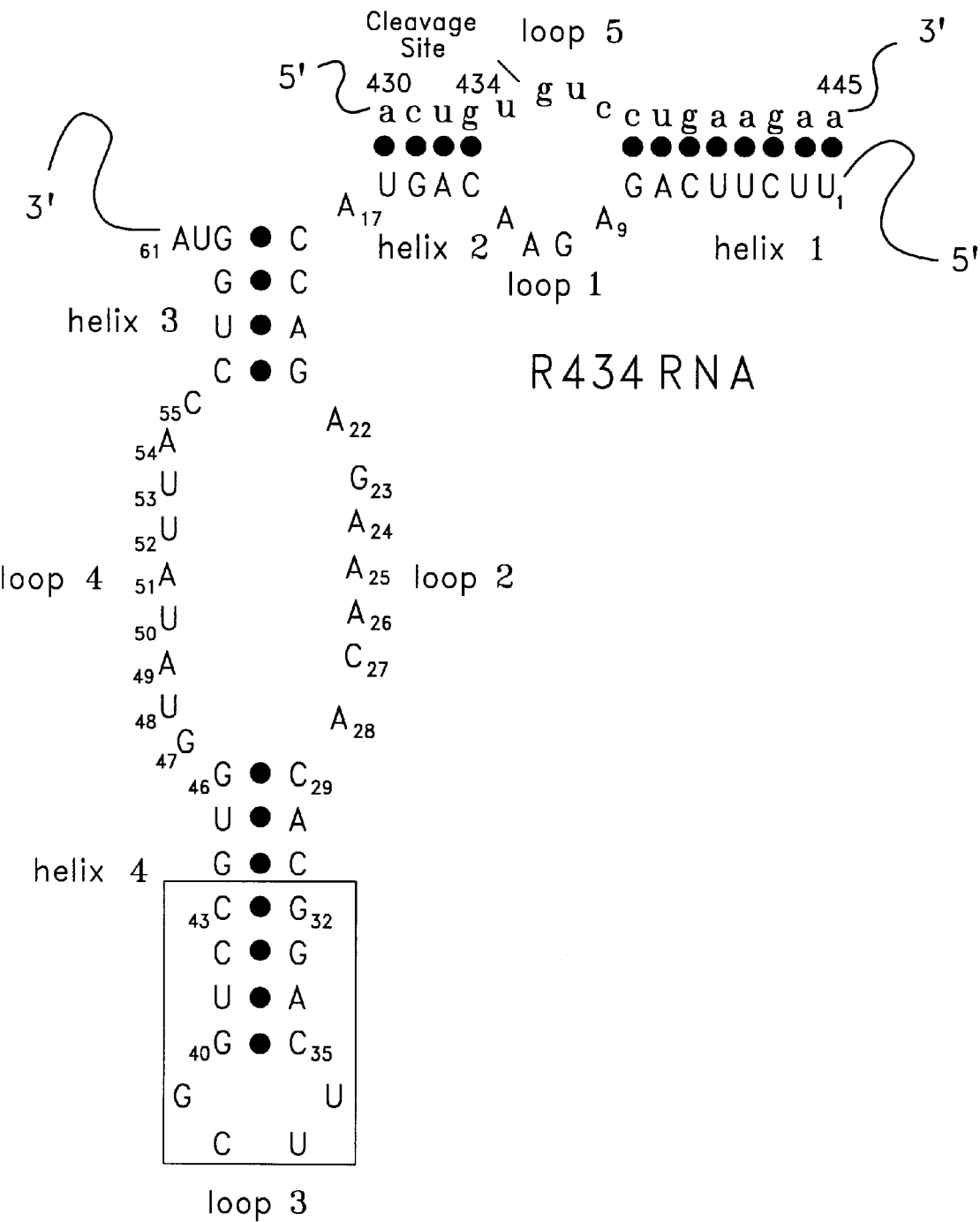
FIG. 2 is a diagram of a hairpin ribozyme for cleavage of HPV-16 E6/E7 mRNA with an optimized helix 1, comprising 8 bp, designed to cleave HPV-16 after position 434 ("cleavage site" indicated by the diagonal line), showing the sequences of the ribozyme (in capital letters) and the substrate (in lower case letters), the regions of base pairing between target substrate (nt 430–445) and ribozyme ("helix 1" and "helix 2"), and the regions of base pairing predicted for the hairpin portion of the ribozyme ("helix 3" and "helix 4").

Potential hairpin ribozyme target sites were identified in the HPV-16 gene sequence for E6/E7 contained within the complete HPV-16 sequence (SEQ ID NO: 1), by using a computer program (e.g., GCG DNA Analysis Package, Genetics Computer Group, Madison, Wis.) to search for 5'-GUC-3' motifs. Several potential cleavage sites were identified in E6 (nt 419, 434, 491, 503 and 514) and E7 (nt 679), and synthetic ribozymes covalently linked to sequences complementary to 15 or 16 nt sequences surrounding the identified potential cleavage sites were produced. The initially synthesized ribozymes were based on the structures of the negative strand of satellite RNA of from the tobacco ringspot virus (-sTRSV) (Hampel & Tritz, 1989, *Biochem.* 28:4929–4933; Haseloff & Gerlach, 1989, *Gene* 82:43–52). Of these synthetic ribozymes, only those having sequences complementary to the E6 sites at nt 419 and 434 were found to significantly cleave substrate RNA (greater than 60% when mixed at a 1:2 molar ratio of ribozyme to substrate RNA). Improved ribozymes were then synthesized for these particular target sequences, in which modifications were introduced in helix 4 (based on the findings of Anderson et al., 1994, *Nucl. Acids Res.* 22:1096–1100). An improved ribozyme structure having a sequence complementary to target sequence of nt 430–445 of E6 mRNA is shown in FIG. 2. Using cell free reactions to optimize the length of helix 1 (in the hybrid formed between the target sequence and the ribozyme complementary sequence), the optimum sequences in the target were those corresponding to the HPV-16 sequence from nt 415–429 (UAACUGUCAAAAGCC; SEQ ID NO:2) and nt 430–445 (ACUGUGUCCUGAAGAA; SEQ ID NO:3). Based on these target sequences, antisense oligonucleotides interacting with these target sequences have the following sequences: GGCUUUUAGAAGUUA (SEQ ID NO:4) and UUCUUCAGAGAACAGU (SEQ ID NO:5), for antisense RNA complementary to nt 415–429 and to nt 430–445 of E6, respectively; and GGCTTTTAGAAGTTA (SEQ ID NO:6) and TTCTTCAGAGAACAGT (SEQ ID NO:7), for antisense DNA complementary to nt 415–429 and to nt 430–445 of E6, respectively.

The ribozyme coding sequences were synthesized and cloned using standard procedures. The coding sequences were synthesized in an automated DNA synthesizer (Expedite 8900, Perceptive Biosystems, Framingham, Mass.) and cloned into a plasmid (pBluescript KS vector, Strategene, La Jolla, Calif.). Ribozyme coding sequences were cloned in cis to complete E6/E7 gene sequences in another plasmid; the E6/E7 and ribozyme sequences were PCR amplified using standard procedures and cloned into another vector (pCR3.1, InVitrogen Corp., San Diego, Calif.) to produce plasmids capable of transcribing ribozymes and target sites in cis. Plasmids were linearized and purified using standard procedures (restriction digestion and QIAquick column, Qiagene Inc., Chatsworth, Calif.) and 1 µg of linear DNA template was incubated with T3 or T7 RNA polymerase, rNTP and α-32P-UTP (Amersham Life Sciences, Arlington Heights, Ill.) to produce ribozyme and/or RNA substrate using standard procedures (e.g., as provided by Ambion Inc., Austin, Tex.). Target RNA was gel purified (6% polyacrylamide/7M urea gel) before use by standard methods.

The active ribozyme that is specific for nt 430–445, designated R434, consists of the ribozyme sequence diagrammed in FIG. 2 (SEQ ID NO:8; UUCUUCAGAGAA-CAGUACCA GAGAAACACACGGACUUCGGUC-CGUGGU AUAUUACCUGGUA). An inactive ribozyme in which the $A_{24}$, $A_{25}$, and $A_{26}$ residues of SEQ ID NO:8 have been replaced with C, G and U, respectively, is referred to as R434i and consists of the ribozyme sequence of SEQ ID NO:9 (UUCUUCAGAGAACAGUACCAGAGCGUCACA CGGACUUCGGUCCGUGGU AUAUUACCUGGUA).

The active ribozyme that contains sequences complementary to E6 nt 415–430 is referred to as R419 and consists of GGCUUUUAGAAGUUAACCAGAGAAACA-CACGGACUUCGGUCCGUGGUA UAUUACCUGGUA (SEQ ID NO:10).

In Vitro Ribozyme Activity

Ribozyme activity was measured in vitro initially at 37° C. in reaction buffer (40 mM Tris-HCl, pH 7.5, 12 mM MgCl$_2$, 2 mM spermidine) containing 25 nM $^{32}$P-labeled ribozyme and 50 nM $^{32}$P-labeled substrate for 60 min; complete characterization was done using similar reactions except that 1 nM $^{32}$P-labeled ribozyme and 30 nM $^{32}$P-labeled substrate (1:30 molar ratio) were incubated for 180 min. Ribozyme expression from linear or covalently-closed templates was accomplished by incubating 1 μl of an in vitro transcription reaction (described above) with 10$^6$ cpm of $^{32}$P-labeled target RNA in 10 μl of reaction mixture. Reactions were stopped by freezing on dry ice; samples were denatured in loading buffer (80% formamide, 0.01% bromophenol blue, 0.01% xylene cyanol) at 65° C. for 10 min and separated by gel electrophoresis (6% polyacrylamide/7M urea gel) using standard methods. Dried gels were exposed to radiographic film (BM-2, Kodak Corp., Rochester, N.Y.) and bands intensities indicative of uncleaved and/or cleaved RNA substrate were quantified using a Phosphorimager 425 (Molecular Dynamics, Sunnyvale, Calif.).

Ribozymes R419 and R434 were active in the in vitro ribozyme reactions in which there was 30-fold excess substrate. The R419 ribozyme had a calculated K$_m$ of 0.098 μM and a k$_{CAT}$ of 0.18 min$^{-1}$; the R434 ribozyme had a calculated K$_m$ of 0.021 μM and a k$_{CAT}$ of 0.08 min$^{-1}$. The catalytic efficiency (k$_{CAT}$/K$_m$) of R434 (3.81 μM$^{-1}$) was twice as high as that of R419 (1.84 μM$^{-1}$). These results show that the antisense oligonucleotide sequences (SEQ ID NO:4 and SEQ ID NO:5) contained in ribozymes R419 and R434 are capable of specifically binding to the HPV-16 target sequences. By analogy, DNA antisense oligonucleotide sequences (SEQ ID NO:6 and SEQ ID NO:7) are equally capable of binding to the HPV-16 target sequences in E6.

Figure 3:
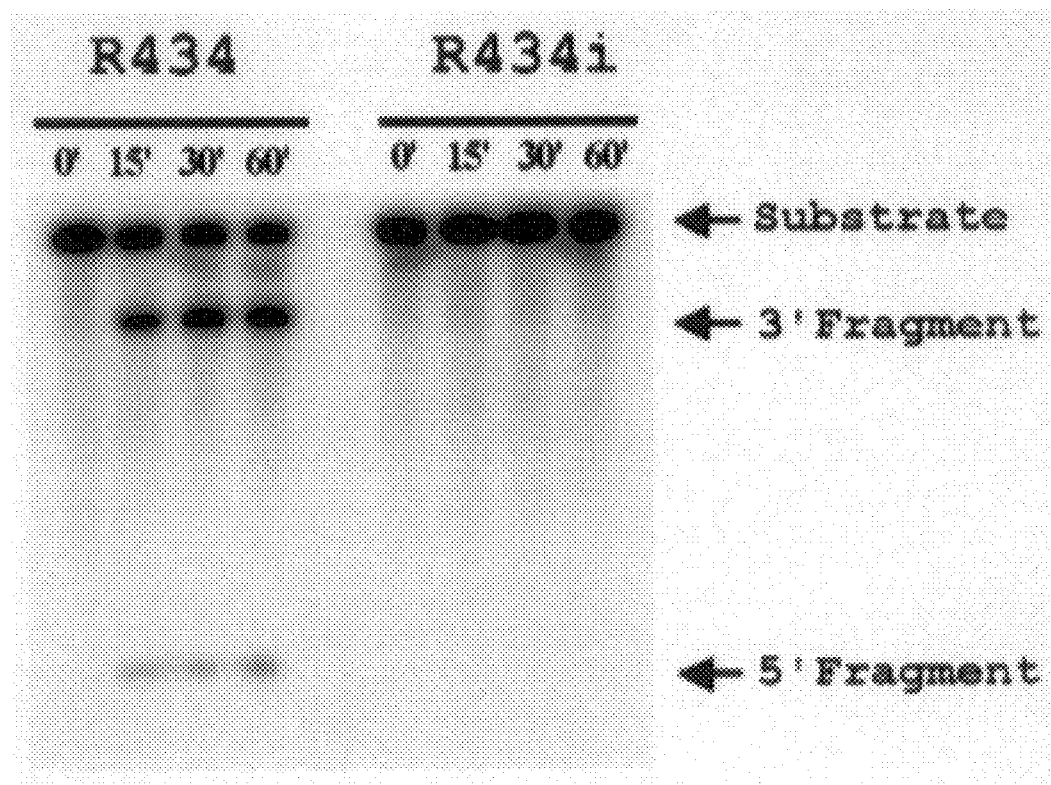
FIG. 3 shows a gel of ribozyme products of the R434 and R434i ribozymes produced by in vitro transcription and incubated with substrate RNA at a 1:2 molar ratio; the arrows at the right show the positions of the uncleaved substrate, and the 3' and 5' fragments produced by substrate cleavage.

The R434i ribozyme is changed in the ribozyme hairpin but contains the same target-recognition site as the R434 ribozyme. These changes abolished catalytic activity of the R343i ribozyme in vitro as shown in FIG. 3, in which aliquots of an in vitro reaction were analyzed at 0, 15, 30 and 60 min. for R434 and R434i ribozyme reactions.

In Vivo Ribozyme Activity in Cultured Human Keratinocytes

Figure 4:
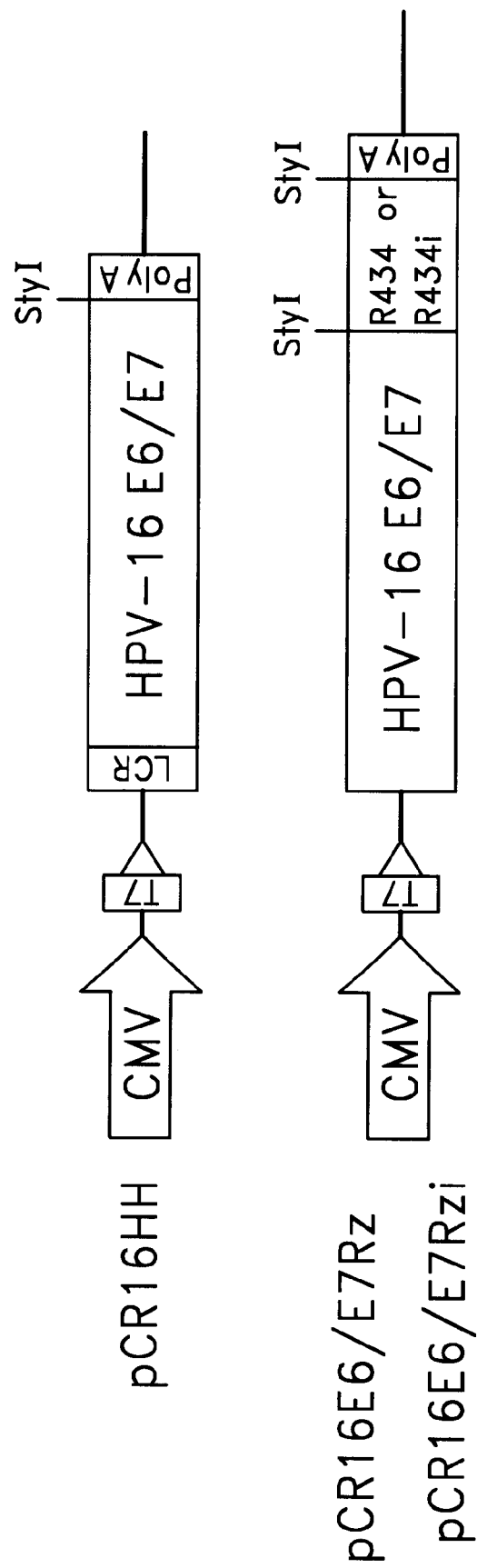
FIG. 4 diagrams the cytomegalovirus promoter/enhancer ("CMV") expression plasmids containing the HPV-16E6/E7 genes only ("pCR16HH"), and with the cis-acting R434 ribozyme or R434i inactive ribozyme coding sequences ("pCR16E6/E7Rz" and "pCR16E6/E7Rzi" respectively).

The R434 and R434i ribozyme sequences were cloned into plasmids for transfection into cells for measurement of in vivo activity. Plasmid pCR16-E6/E7RZ contains the E6/E7 gene sequences linked in cis to the 5' end of enzymatically-active ribozyme R434 sequence, and plasmid pCR16-E6/E7RZi contains the E6/E7 gene sequences linked in cis to the 5' end of enzymatically-inactive ribozyme R434i sequence. In both plasmids, the constructs were under the control of the cytomegalovirus (CMV) promoter/enhancer sequences as diagramed in FIG. 4. Control plasmids ("pCR16HH") contained the E6/E7 gene sequences under the control of the CMV promoter/enhancer sequences but without any ribozyme sequences.

Normal human keratinocytes (HKc) from neonatal foreskins were cultured in MCDB151-LB medium using standard methods (Pirisi et al., 1988, *Carcinogen.* 9:1573–1579) and transfected with 10 μg of plasmid DNA using standard lipofection methods (Lipofectin, Life Technologies Inc., Gaithersburg, Md.; Alvarez-Salas et al., 1995, *Cancer Lett.* 91:85–92). Transfected cells were grown in the presence of 200 μg/ml of G418 for two weeks (or four days for immortalization studies) and growth rates were determined in standard six-well plates (10$^6$ cells/well) in triplicate; cells were counted at the end of the incubation period (Coulter Counter ZM, Coulter Electronics Inc., Hialeah, Fla.).

Figure 5:
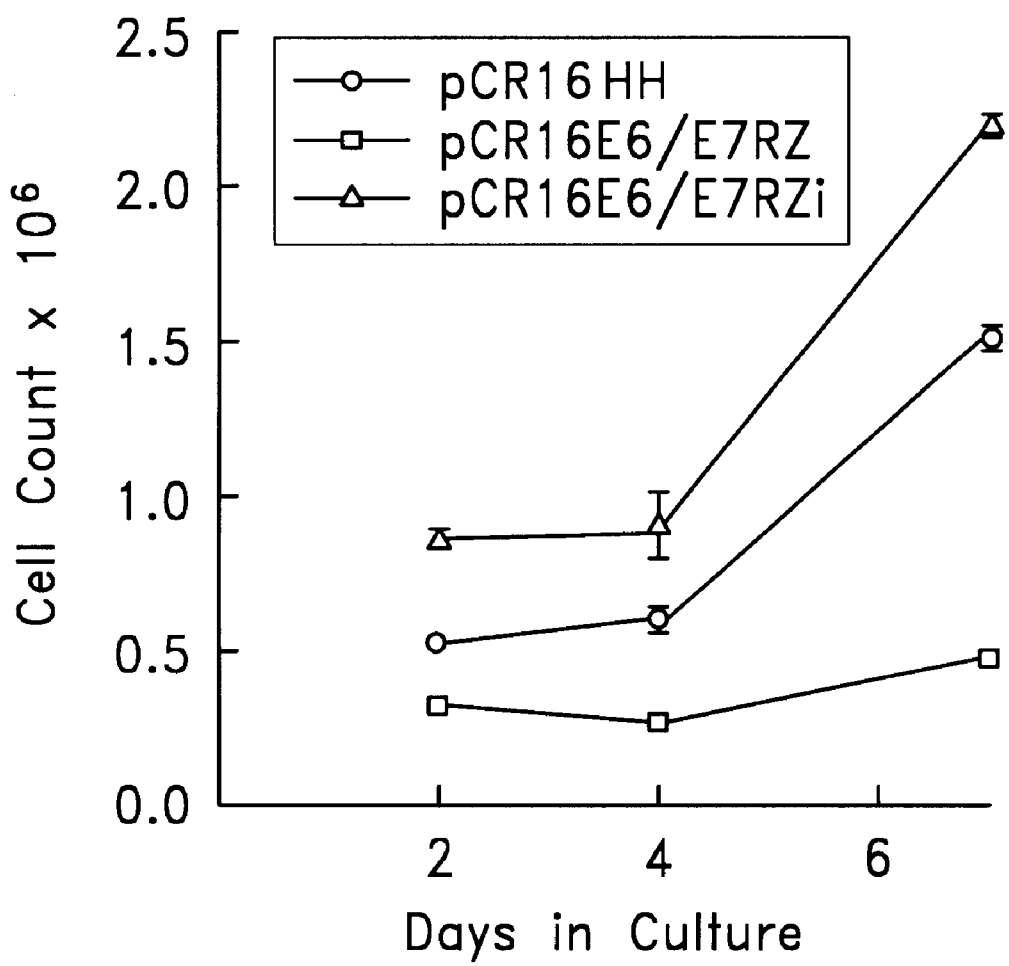
FIG. 5 shows a graph of cell growth of normal human keratinocytes (HKc) (cell count on the Y-axis) over 2 to 7 days in culture (X-axis) for HKc transfected with the control plasmid, pCR16HH (-○-), the active ribozyme construct, pCR16E6/E7RZ (-□-) and the inactive ribozyme construct, pCR16E6/E7RZi (-Δ-). construct

Following transfection of HKc with the plasmid constructs, cell growth was assayed at 2 to 7 days post-transfection (shown in FIG. 5). HKc transfected with the active ribozyme construct (pCR16E6/E7RZ, -□-) grew significantly slower than cells transfected with the control plasmid (pCR16HH, -○-) or the inactive ribozyme (pCR16E6/E7RZi, -Δ-) construct. The latter two were capable of expressing the E6/E7 gene products, whereas the active ribozyme would have limited E6/E7 gene expression. To confirm this, a reverse transcription-polymerase chain reaction (RT-PCR) assay was performed to detect the products of ribozyme cleavage.

The RT-PCR assay was performed as follows. Total RNA was purified from the cultured cells (Rneasy Kit, Quigen) using standard methods. HPV-16 E6/E7 cDNA was produced from 1 μg of total RNA using standard methods (Superscript II One Shot Kit, Life Technologies). To produce differential sized bands for cleaved and uncleaved E6/E7 mRNA, the upper PCR primers were SEQ ID NO:11 (CAGCAATACAACAAACCG) and SEQ ID NO:12 (CACGTAGAAACCCAGC), flanking the R434 target site (nt 371–388 and nt 537–554, respectively), and the lower primer was SEQ ID NO:13 (TAGATTATGGTTTCTGAGAACA), hybridizing in the E7 gene (nt 862–841). Standard PCR conditions were used (as supplied by Strategene, La Jolla, Calif.) with the following times and temperatures. The first strand cDNA was synthesized for 30 min at 45° C., followed by denaturation (92° C. for 2 min) and 35 PCR cycles of: denaturation (92° C. for 1 min), hybridization of primers (45° C. for 45 sec) and polymerization (72° C. for 1 min). This PCR amplification produced two products: an uncleaved product of 492 bp (amplified by SEQ ID NO:11 and SEQ ID NO:13) and an internal control product of 326 bp (amplified by SEQ ID NO:12 and SEQ ID NO:13). A control PCR reaction under the same conditions but with primers specific for an endogenous β-actin gene (SEQ ID NO:14: TGACGGGGTCACCCACACTGTGCCCCATCTA, and SEQ ID NO:15: CTAAGAAGCATTTGCGGTGGACGATGGAGGG) was used as a control to produce a band of 661 bp. Amplified products were separated on a 1.5% agarose gel and visualized with long-wave UV after ethidium bromide staining.

Figure 6:
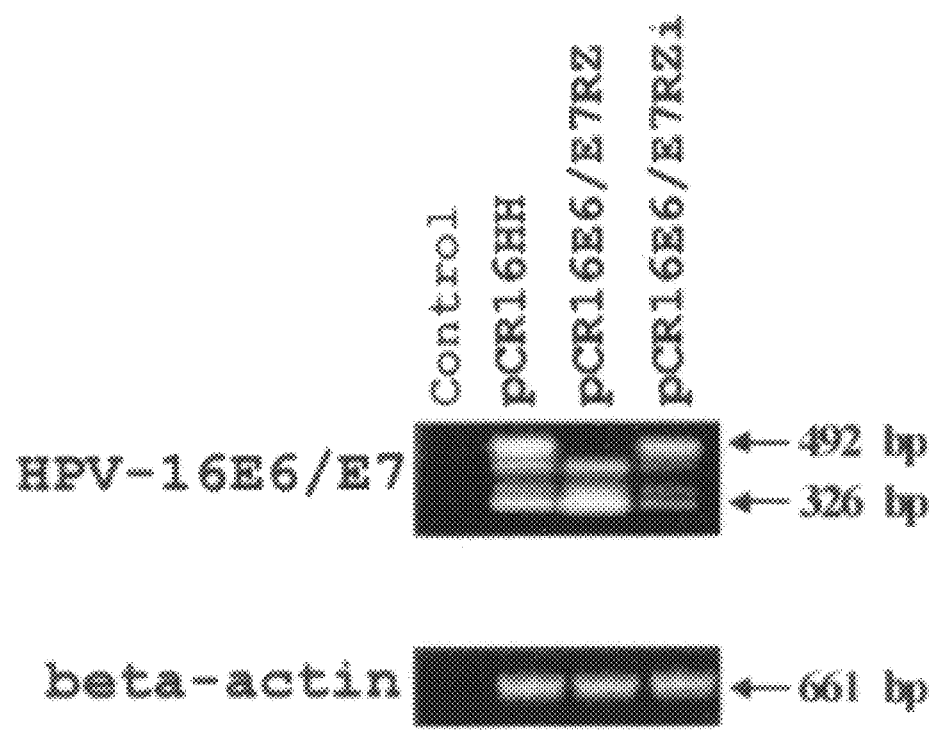
FIG. 6 shows an agarose gel separation of the products of a RT-PCR assay specific for HPV-16E6/E7 mRNA. HKc were transfected with the E6/E7 construct without any ribozyme sequences (pCR16HH), the active ribozyme construct (pCR16E6/E7RZ), and the inactive ribozyme construct (pCR16E6/E7RZi); the negative "Control" is a RT-PCR reaction run without reverse transcriptase. The lower panel shows that all cells produced the 661 bp β-actin band; the upper panel shows the 492 bp uncleaved E6/E7 transcript band and an internal control band of 326 bp.

As shown in FIG. 6, all of the transfected cells produced the 661 bp β-actin control band. The control transfected (pCR16HH) cells and the inactive ribozyme construct (pCR16E6/E7RZi) transfected cells produced both the 492 bp and 326 bp products showing the presence of full-length E6/E7 transcripts, whereas the active ribozyme construct (pCR16E6/E7RZ) produced no detectable amount of the 492 bp band, indicating cleavage. These results support the finding that the decreased growth rate of the HKc transfected with the active ribozyme construct (pCR16E6/E7RZ) was due to the inhibition of E6/E7 gene expression.

Inactive Ribozyme Has In Vivo Antisense Activity

The effects of long-term expression of the E6/E7 genes with or without antisense containing ribozyme were investigated using transfected HKc as above, but maintained for up to 8 weeks in culture with standard cell culture medium after an initial G418 drug selection of four days. By the end of the 8-week incubation, HKc transfected with a non-immortalizing gene (bacterial β-galactosidase, as a negative control) had senesced and detached. Therefore, mostiy immortal cells were present in the cell cultures at the end of the 8-week incubation.

Figure 7:
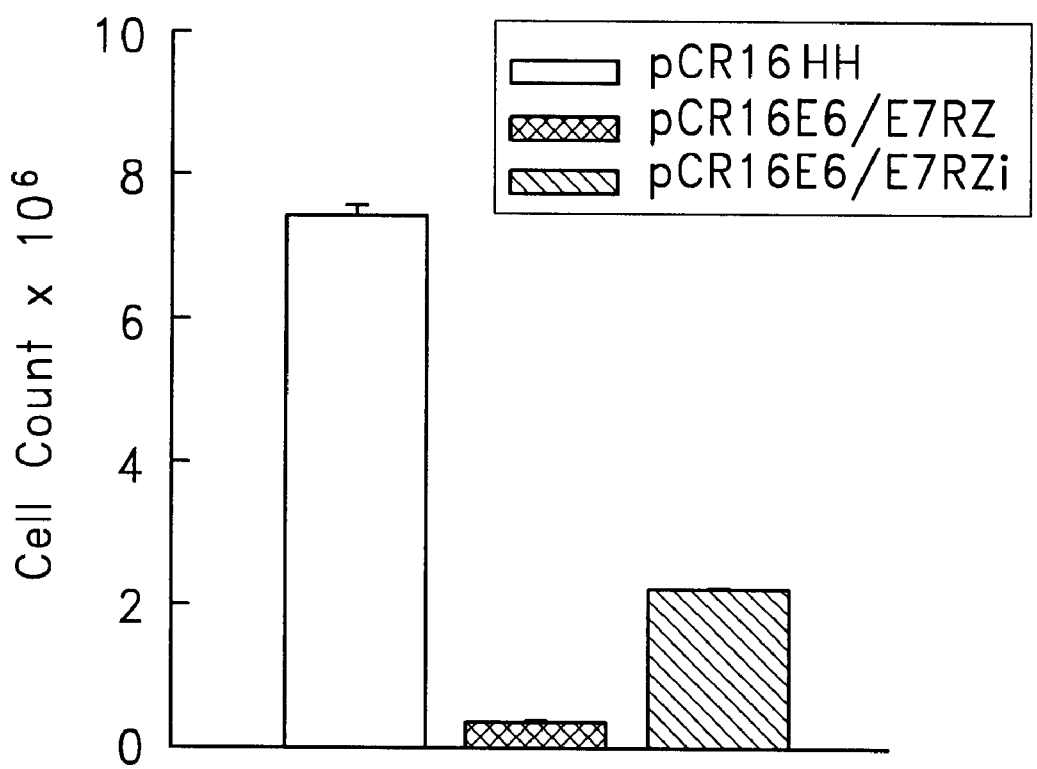
FIG. 7 is a graph showing the cell counts (Y-axis) for HKc transfected with the E6/E7 construct without any ribozyme sequences (pCR16HH, left bar), the active ribozyme construct (pCR16E6/E7RZ, middle bar), and the inactive ribozyme construct (pCR16E6/E7RZi, right bar) at 8 weeks of growth following transfection.

As shown in FIG. 7, cells transfected with the E6/E7 control (pCR16HH) were efficiently immortalized. Cells transfected with the active ribozyme construct (pCR16E6/E7RZ) showed little survival (about 10% relative to the control), as expected because of the limited E6/E7 gene expression. Cells transfected with the inactive ribozyme construct (pCR16E6/E7RZi) also showed decreased survival compared to the control, indicative that the antisense oligonucleotide portion of the construct, even in the absence of ribozyme activity, significantly inhibited E6/E7 gene expression. The lack of E6/E7 gene expression was confirmed using the RT-PCR assay which did not detect full length (492 bp) E6/E7 transcripts in either the cells transfected with active or inactive ribozyme constructs (pCR16E6/E7RZ or pCR16E6/E7RZi). These results also show the inhibitory activity in vivo of the antisense E6 oligonucleotide moiety of the pCR16E6/E7RZi construct.

The antisense oligonucleotides (SEQ ID NO:6, SEQ ID NO:7) corresponding to the antisense sequences contained in the ribozymes (SEQ ID NO:4, SEQ ID NO:5) are synthesized as normal phosphodieter bond-linked oligonucleotides and phosphorothioate oligonucleotides to inhibit E6/E7 gene expression in human cells infected with HPV. The phosphorothioate antisense oligonucleotides (PS-oligonucleotides) are synthesized using standard methods (Agrawal et al., 1997, *Proc. Natl. Acad. Sci. USA* 94:2620–2625; Agrawal, 1996, TIBTECH 14:376–387). That is, the oligonucleotides are synthesized in which one of the non-bridging oxygens of the internucleotide phosphodiester linkages is replaced with sulfur; the synthesis is done using methods that produce a diastereomeric mixture of Rp and Sp PS-oligonucleotides. HKc that have been shown to contain HPV sequences or suspected of containing HPV sequences due to their source of origin (e.g., cervical cancer cells) are then transfected with about 25 nM to about 500 nM concentration, preferably about 200 nM concentrations, of oligonucleotides and PS-oligonucleotides, using lipofection as described above or any well known transfection methodology. Cells of the same origin as those transfected are used as a source of purified RNA, essentially as described above. Transfected cells are allowed to grow for 2–10 days in culture and then RNA is similarly isolated from them. E6 transcripts are assayed in the untransfected control cells and the antisense-oligonucleotide and antisense PS-oligonucleotide transfected cells using the RT-PCR assay substantially as described above. The amount of E6 transcript detected in transfected and untransfected cells of the same origin are compared and quantified.

In untransfected control cells, E6 transcripts are present in most cells known to harbor HPV sequences and in most cervical cancer cells isolated from invasive cancers. In the matched cells for each sample transfected with the antisense oligonucleotides and antisense PS-oligonucleotides, there is measurably less E6 transcript detected compared to the matched control. The inhibition of E6 gene expression ranges from about 10% to about 95%, depending on the combination of the cells used and the antisense oligonucleotide or PS-oligonucleotide. Some cells show about 70% to about 80% inhibition, whereas others show about 40% to about 50% inhibition, and still others show about 10% to about 25% inhibition of E6 gene expression compared to the matched untransfected control cells. In all cells, a positive control (e.g., β-actin gene expression (detected using the RT-PCR assay and primers of SEQ ID NO:14 and SEQ ID NO:15, as described above) varies by less than about 1% to about 5% from the HPV-antisense transfected cells and their matched untransfected control cells.

Similarly, antisense oligonucleotide and PS-oligonucleotide having sequences of SEQ ID NO:17 (TTCTTCAGAGAACAGTGGCTTTTGACAGTTA; corresponding to the antisense of the RNA sequence SEQ ID NO:16: UUCUUCAGAGAACAGUGGCUUUUGACAGUUA), representing the antisense DNA to nt 415 to 445 of HPV-16 are also synthesized using standard methods. Similarly the longer antisense oligonucleotide and PS-oligonucleotide are used in transfections of HKc, substantially as described above. The results of RT-PCR assays to determine the relative amounts of E6 transcripts in antisense oligonucleotide and PS-oligonucleotide transfected cells, compared to untransfected matched control cells, show somewhat less inhibition of E6 transcripts in the transfected cells compared to the smaller antisense oligonucleotide and PS-oligonucleotides described above. That is, about 0% to about 50% inhibition of E6 transcripts is detected in the tested cells. This lower level of inhibition may reflect less efficient transfection with the longer antisense oligonucleotide and PS-oligonucleotide.

When proliferation of the transfected cells (with any of the above-described antisense oligonucleotides and PS-oligonucleotides) and the matched untransfected control cells are compared using cell culture times of 1 to 5 days (starting at day 0, with about $10^6$ cells/well of a standard 6-well culture pjlate and standard tissue culture conditions), the untransfected control cells generally show considerably more cell growth during the growth period than the matched transfected cells. The degree of proliferation inhibition is best seen at days 1 to 3, with some transfected cells showing approximately the same rate of cell proliferation as the matched control cells by day 5 after transfection. Some transfected cells show no inhibition of cell growth at any point in the testing period. Others show about 5% to about 40% inhibition of growth, depending on the cell line and the antisense oligonucleotide used. Retransfection at day 4, with those cells that initially show cell proliferation, reinstitutes the inhibition caused by the antisense oligonucleotides.

Similar inhibition results are obtained with antisense oligonucleotide sequences (SEQ ID NO:6, SEQ ID NO:7, and SEQ ID NO:17) synthesized as mixed backbone oligonucleotides, having 2'-O-methylnucleoside phophodiester bonds in place of phosphorothioate bonds in some positions, and oligonucleotides synthesized with ends of 2'-O-methylnucleosides, both types synthesized using known methods (Agrawal et al., 1997, *Proc. Natl. Acad. Sci. USA* 94:2620–2625). The mixed backbone antisense oligonucleotides, synthesized as racemic mixtures, are preferable to completely PS-oligonucleotides because of reduced toxicity to cells exhibited by the mixed backbone oligonucleotides.

Similar tests are performed with the antisense oligonucleotide sequences (SEQ ID NO:6, SEQ ID NO:7, and SEQ ID NO:17) synthesized as analogs using standard methods. The analogs synthesized are methylphosphonates (Miller et al., 1993, in *Antisense Research and Applications*, pp.189–203, Crooke & Lebleu, eds., CRC Press; Sarin et al., 1988, *Proc. Natl. Acad. Sci. USA* 85:7448–7451); phosphoramidates (Dagle et al., 1991, *Nucl. Acids Res.* 19(8):1805–1810; Froehler et al., 1988, *Nucl. Acids Res.* 16(11):4831–4839; Tanaka et al., 1987, *Nucl. Acids Res.* 15(15):6209–6224); phosphorodithioates (Marshall et al., 1992, *Proc. Natl. Acad. Sci. USA* 89:6265–6269), and N3'→-P5'-phosphoramidates (Gryznov et al., *Nucl. Acids Res.* 24:1508–1514; Escude et al., 1996, *Proc. Natl. Acadc Sci. USA* 93(9):4365–4369; Chen et al., 1995, *Nucl. Acids Res.* 23(14):2661–2668). Analogs of the antisense oligoribonucleotides (SEQ ID NO:4, SEQ ID NO:5 and SEQ ID NO:16) are synthesized using known methods to produce oligoribonucleotide phosphorothioates (Agrawal et al., 1992, *Ann. New York Acad Sci.* 660:2–10) and their 2'-O-alkyl analogs (Metelev et al., 1994, *Bioorg. Med. Chem. Lett.* 4:2929–2934; McKay et al., 1996, *Nucl. Acids Res.* 24:411–417; Monia et al., *J Biol. Chem.* 268:14514–14522) and 2'-O-methylribonucleotide methylphosphonates (Kean et al., 1995, *Biochemistry* 34:14617–14620). All of the above-cited methods are known in the art and can readily be practiced by those skilled in the art; however, details regarding synthesis methods contained in the references cited herein are hereby incorporated by reference.

Antitumor Activity of Antisense Therapeutics in a Mouse Model

The antisense oligonucleotides, antisense PS-oligonucleotides, mixed backbone antisense oligonucleotides, oligonucleotides having ends of 2'-O-methylnucleosides, and the oligonucleotide analogs or oligoribonucleotide analogs are used in a mouse model in which tumor cells that are HPV-positive are injected into mice (e.g., i.p. at $10^3$ to $10^8$ cells/mouse) where they produce solid tumors or ascites. Preferred tumor cells are those isolated from spontaneous cervical carcinomas that are HPV positive (16 cell lines of this type are currently available for use). The mice are injected with 100 μg to 1,000 μg per day of the antisense therapeutic (i.p., s.c. or i.v.) before, simultaneously with or after injection of the human tumor cells (using protocols substantially as described in Skorski et al., *Proc. Natl. Acad Sci. USA*, 1997, 94(8):3966–3971). Control mice receive only the tumor cells. The mice are monitored for survival times and, using standard assay techniques, for production of solid tumors and/or ascites at daily to weekly intervals from 1 day to 5 months post-injection of the tumor cells.

Injection of the antisense therapeutics one day before or simultaneously with injection of the tumor cells shows that some of the antisense therapeutics have protective effects and prevent tumor development that otherwise occurs in the untreated controls injected with tumor cells. That is, treatment of mice with some of the antisense therapeutics entirely inhibits tumor cell growth or significantly slows growth of tumors or ascites compared to control mice that receive the same number of injected tumor cells but no antisense treatment. For those antisense therapeutics that show antitumor activity in preliminary tests, daily injections of 100, 300 and 900 μg are subsequently tested to determine optimum antitumor activity and toxicity levels resulting from daily injections.

Injection of the antisense therapeutics at 1 day to 4 weeks after injection of the tumor cells shows that some of the antisense therapeutics are capable of limiting or eliminating tumors that otherwise grow in the untreated controls. Generally, antisense treatment is more effective, both in terms of long-term survival and inhibition of tumor cell proliferation, when treatment begins early after injection of tumor cells (i.e., within 1 to 2 weeks) and when mice receive repeated injections of the antisense therapeutic (e.g., daily or weekly dosages) during the test period. Also, the analogs (e.g., mixed backbone oligonucleotides and methylphosphonates, phosphoramidates, phosphorodithioates, or N3'→P5'-phosphoramidates) are generally more effective at lower concentrations (e.g., 100 μg to 500 μg/day) than the corresponding unmodified antisense oligonucleotides.

In other animal models, mice showing spontaneous growth of cervical cancers are treated by s.c. injection or painting of the cervical tumor with the antisense therapeutics described herein. Some tumors treated with some of the antisense therapeutics show a decrease in tumor growth or remission of the tumor. In general, the antisense therapeutics that are mixed backbone oligonucleotides or other analogs (e.g., methylphosphonates, phosphoramidates, phosphorodithioates, or N3'→P5'-phosphoramidates) are generally more effective at lower concentrations (e.g., 25 nM to 100 nM/day) than the corresponding unmodified antisense oligonucleotides.

Similarly, analogs of antisense oligoribonucleotides of SEQ ID NO:4, SEQ ID NO:5 and SEQ ID NO:16, in which the analogs are oligoribonucleotide phosphorothioates, 2'-O-alkyl oligoribonucleotide phosphorothioates or 2'-O-methylribonucleotide methylphosphonates, are tested to antitumor activity in the assays described above. Some of the antisense oligoribonucleotide analogs also show significant antitumor activity in vitro and in vivo.

While particular embodiments of the invention have been described in detail, it will be apparent to those skilled in the art that these embodiments are exemplary rather than limiting, and the true scope of the invention is defined by the claims that follow.

---

What is claimed is:

1. An antisense oligonucleotide analog comprising a sequence complementay to substrate sequence UAACUGUCAAAAGCC (SEQ ID NO:2) in the HPV-16 E6/E7 genes, wherein said analog: contains at least one phosphorothioate bond, is a mixed backbone antisense oligonucleotide in which at least one phosphodiester bond is replaced with a phosphorothioate and further contains at least one 2'-O-methylnucleoside, contains at least one 5' or 3' end 2'-O-methylnucleoside moiety, is a methylphosphonate, is a phosphoramidate, is a phosphorodithioate, or is a N3'→P5'-phosphoramidate.

* * * * *

SEQUENCE LISTING (1) GENERAL INFORMATION:

(iii) NUMBER OF SEQUENCES: 17

(2) INFORMATION FOR SEQ ID NO: 1:

(i) SEQUENCE CHARACTERISTICS:
      (A) LENGTH: 7904 base pairs
      (B) TYPE: nucleic acid
      (C) STRANDEDNESS: double
      (D) TOPOLOGY: linear (ii) MOLECULE TYPE: Genomic DNA (xi) SEQUENCE DESCRIPTION: SEQ ID NO: 1:

```
ACTACAATAA TTCATGTATA AAACTAAGGG CGTAACCGAA ATCGGTTGAA CCGAAACCG      60

TTAGTATAAA AGCAGACATT TTATGCACCA AAAGAGAACT GCAATGTTTC AGGACCCA     120

GGAGCGACCC AGAAAGTTAC CACAGTTATG CACAGAGCTG CAAACAACTA TACATGAT    180

AATATTAGAA TGTGTGTACT GCAAGCAACA GTTACTGCGA CGTGAGGTAT ATGACTTT    240

TTTTCGGGAT TTATGCATAG TATATAGAGA TGGGAATCCA TATGCTGTAT GTGATAAA    300

TTTAAAGTTT TATTCTAAAA TTAGTGAGTA TAGACATTAT TGTTATAGTT TGTATGGA    360

AACATTAGAA CAGCAATACA ACAAACCGTT GTGTGATTTG TTAATTAGGT GTATTAAC    420

TCAAAAGCCA CTGTGTCCTG AAGAAAGCA AAGACATCTG GACAAAAAGC AAAGATTC     480

TAATATAAGG GGTCGGTGGA CCGGTCGATG TATGTCTTGT TGCAGATCAT CAAGAACA    540

TAGAGAAACC CAGCTGTAAT CATGCATGGA GATACACCTA CATTGCATGA ATATATGT    600

GATTTGCAAC CAGAGACAAC TGATCTCTAC TGTTATGAGC AATTAAATGA CAGCTCAG    660

GAGGAGGATG AAATAGATGG TCCAGCTGGA CAAGCAGAAC CGGACAGAGC CCATTACA    720

ATTGTAACCT TTTGTTGCAA GTGTGACTCT ACGCTTCGGT TGTGCGTACA AAGCACAC    780

GTAGACATTC GTACTTTGGA AGACCTGTTA ATGGGCACAC TAGGAATTGT GTGCCCCA    840

TGTTCTCAGA AACCATAATC TACCATGGCT GATCCTGCAG GTACCAATGG GGAAGAGG    900

ACGGGATGTA ATGGATGGTT TTATGTAGAG CTGTAGTGG AAAAAAAAC AGGGGATG     960

ATATCAGATG ACGAGAACGA AAATGACAGT GATACAGGTG AAGATTTGGT AGATTTT    1020

GTAAATGATA ATGATTATTT AACACAGGCA GAAACAGAGA CAGCACATGC GTTGTTT    1080

GCACAGGAAG CAAAACAACA TAGAGATGCA GTACAGGTTC TAAAACGAAA GTATTTG    1140

GTCCACTTAG TGATATTAGT GGATGTGTAG ACAATAATAT TAGTCCTAGA TTAAAAG    1200

TATGTATAGA AAAACAAAGT AGAGCTGCAA AAAGGAGATT ATTTGAAAGC GAAGACA    1260

GGTATGGCAA TACTGAAGTG GAAACTCAGC AGATGTTACA GGTAGAAGGG CGCCATG    1320

CTGAAACACC ATGTAGTCAG TATAGTGGTG GAAGTGGGGG TGGTTGCAGT CAGTACA    1380

GTGGAAGTGG GGGAGAGGGT GTTAGTGAAA GACACACTAT ATGCCAAACA CCACTTA    1440

ATATTTTAAA TGTACTAAAA ACTAGTAATG CAAAGGCAGC AATGTTAGCA AAATTTA    1500

AGTTATACGG GGTGAGTTTT TCAGAATTAG TAAGACCATT TAAAAGTAAT AAATCAA    1560

GTTGCGATTG TGTATTGCT GCATTTGGAC TTACACCCAG TATAGCTGAC AGTATAA     1620

CACTATTACA ACAATATTGT TTATATTTAC ACATTCAAAG TTTAGCATGT TCATGGG    1680

TGGTTGTGTT ACTATTAGTA AGATATAAAT GTGGAAAAAA TAGAGAAACA ATTGAAA    1740

TGCTGTCTAA ACTATTATGT GTGTCTCCAA TGTGTATGAT GATAGAGCCT CCAAAAT    1800

GTAGTACAGC AGCAGCATTA TATTGGTATA AACAGGTAT ATCAAATATT AGTGAAG     1860

ATGGAGACAC GCCAGAATGG ATACAAAGAC AAACAGTATT ACAACATAGT TTTAATG    1920

GTACATTTGA ATTATCACAG ATGGTACAAT GGGCCTACGA TAATGACATA GTAGACG    1980

GTGAAATTGC ATATAAATAT GCACAATTGG CAGACACTAA TAGTAATGCA AGTGCCT    2040

TAAAAAGTAA TTCACAGGCA AAAATTGTAA AGGATTGTGC AACAATGTGT AGACATT    2100

AACGAGCAGA AAAAAAACAA ATGAGTATGA GTCAATGGAT AAAATATAGA TGTGATA    2160

TAGATGATGG AGGTGATTGG AAGCAAATTG TTATGTTTTT AAGGTATCAA GGTGTAG    2220
```

```
TTATGTCATT TTTAACTGCA TTAAAAAGAT TTTTGCAAGG CATACCTAAA AAAAATT      2280

TATTACTATA TGGTGCAGCT AACACAGGTA AATCATTATT TGGTATGAGT TAATGA       2340

TTCTGCAAGG GTCTGTAATA TGTTTTGTAA ATTCTAAAAG CCATTTTTGG TTACAAC      2400

TAGCAGATGC CAAAATAGGT ATGTTAGATG ATGCTACAGT GCCCTGTTGG AACTACA      2460

ATGACAATTT AAGAAATGCA TTGGATGGAA ATTTAGTTTC TATGGATGTA AAGCATA      2520

CATTGGTACA ACTAAAATGC CCTCCATTAT TAATTACATC TAACATTAAT GCTGGTA      2580

ATTCTAGGTG GCCTTATTTA CATAATAGAT TGGTGGTGTT TACATTTCCT AATGAGT      2640

CATTTGACGA AAACGGAAAT CCAGTGTATG AGCTTAATGA TAAGAACTGG AAATCCT      2700

TCTCAAGGAC GTGGTCCAGA TTAAGTTTGC ACGAGGACGA GGACAAGGAA AACGATG      2760

ACTCTTTGCC AACGTTTAAA TGTGTGTCAG GACAAAATAC TAACACATTA TGAAAAT      2820

AGTACAGACC TACGTGACCA TATAGACTAT TGGAAACACA TGCGCCTAGA ATGTGCT      2880

TATTACAAGG CCAGAGAAAT GGGATTTAAA CATATTAACC ACCAAGTGGT GCCAACA      2940

GCTGTATCAA AGAATAAAGC ATTACAAGCA ATTGAACTGC AACTAACGTT AGAAACA      3000

TATAACTCAC AATATAGTAA TGAAAAGTGG ACATTACAAG ACGTTAGCCT TGAAGTG      3060

TTAACTGCAC CAACAGGATG TATAAAAAAA CATGGATATA CAGTGGAAGT GCAGTTT      3120

GGAGACATAT GCAATACAAT GCATTATACA AACTGGACAC ATATATATAT TTGTGAA      3180

GCATCAGTAA CTGTGGTAGA GGGTCAAGTT GACTATTATG GTTTATATTA TGTTCAT      3240

GGAATACGAA CATATTTTGT GCAGTTTAAA GATGATGCAG AAAAATATAG TAAAAAT      3300

GTATGGGAAG TTCATGCGGG TGGTCAGGTA ATATTATGTC CTACATCTGT GTTTAGC      3360

AACGAAGTAT CCTCTCCTGA AATTATTAGG CAGCACTTGG CCAACCACCC CGCCGCG      3420

CATACCAAAG CCGTCGCCTT GGGCACCGAA GAAACACAGA CGACTATCCA GCGACCA      3480

TCAGAGCCAG ACACCGGAAA CCCCTGCCAC ACCACTAAGT TGTTGCACAG AGACTCA      3540

GACAGTGCTC CAATCCTCAC TGCATTTAAC AGCTCACACA AAGGACGGAT TAACTGT      3600

AGTAACACTA CACCCATAGT ACATTTAAAA GGTGATGCTA ATACTTTAAA ATGTTTA      3660

TATAGATTTA AAAAGCATTG TACATTGTAT ACTGCAGTGT CGTCTACATG GCATTGG      3720

GGACATAATG TAAAACATAA AAGTGCAATT GTTACACTTA CATATGATAG TGAATGG      3780

CGTGACCAAT TTTTGTCTCA AGTTAAAATA CCAAAAACTA TTACAGTGTC TACTGGA      3840

ATGTCTATAT GACAAATCTT GATACTGCAT CCACAACATT ACTGGCGTGC TTTTTGC      3900

GCTTTGTGTG CTTTTGTGTG TCTGCCTATT AATACGTCCG CTGCTTTTGT CTGTGTC      3960

ATACACATCA TTAATAATAT TGGTATTACT ATTGTGGATA ACAGCAGCCT CTGCGTT      4020

GTGTTTATT GTATATATTA TATTTGTTTA TATACCATTA TTTTTAATAC ATACACA      4080

ACGCTTTTTA ATTACATAAT GTATATGTAC ATAATGTAAT TGTTACATAT AATTGTT      4140

TACCATAACT TACTATTTTT TCTTTTTTAT TTTCATATAT AATTTTTTTT TTTGTTT      4200

TGTTTGTTTT TTAATAAACT GTTATTACTT AACAATGCGA CACAAACGTT CTGCAAA      4260

CACAAAACGT GCATCGGCTA CCCAACTTTA TAAAACATGC AAACAGGCAG GTACATG      4320

ACCTGACATT ATACCTAAGG TTGAAGGCAA AACTATTGCT GAACAAATAT TACAATA      4380

AAGTATGGGT GTATTTTTTG GTGGGTTAGG AATTGGAACA GGGTCGGGTA CAGGCGG      4440

CACTGGGTAT ATTCCATTGG GAACAAGGCC TCCCACAGCT ACAGATACAC TTGCTCC      4500

AAGACCCCCT TTAACAGTAG ATCCTGTGGG CCCTTCTGAT CCTTCTATAG TTTCTTT      4560

GGAAGAAACT AGTTTTATTG ATGCTGGTGC ACCAACATCT GTACCTTCCA TTCCCCC      4620
```

```
TGTATCAGGA TTTAGTATTA CTACTTCAAC TGATACCACA CCTGCTATAT TAGATAT      4680

TAATACTGTT ACTACTGTTA CTACACATAA TAATCCCACT TTCACTGACC CATCTGT      4740

GCAGCCTCCA ACACCTGCAG AAACTGGAGG GCATTTTACA CTTTCATCAT CCACTAT      4800

TACACATAAT TATGAAGAAA TTCCTATGGA TACATTTATT GTTAGCACAA ACCCTAA      4860

AGTAACTAGT AGCACACCCA TACCAGGGTC TCGCCCAGTG GCACGCCTAG GATTATA      4920

TCGCACAACA CAACAGGTTA AAGTTGTAGA CCCTGCTTTT GTAACCACTC CCACTAA      4980

TATTACATAT GATAATCCTG CATATGAAGG TATAGATGTG GATAATACAT TATATTT      5040

TAGTAATGAT AATAGTATTA ATATAGCTCC AGATCCTGAC TTTTTGGATA TAGTTGC      5100

ACATAGGCCA GCATTAACCT CTAGGCGTAC TGGCATTAGG TACAGTAGAA TTGGTAA      5160

ACAAACACTA CGTACTCGTA GTGGAAAATC TATAGGTGCT AAGGTACATT ATTATTA      5220

TTTAAGTACT ATTGATCCTG CAGAAGAAAT AGAATTACAA ACTATAACAC CTTCTAC      5280

TACTACCACT TCACATGCAG CCTCACCTAC TTCTATTAAT AATGGATTAT ATGATAT      5340

TGCAGATGAC TTTATTACAG ATACTTCTAC AACCCCGGTA CCATCTGTAC CCTCTAC      5400

TTTATCAGGT TATATTCCTG CAAATACAAC AATTCCTTTT GGTGGTGCAT ACAATAT      5460

TTTAGTATCA GGTCCTGATA TACCCATTAA TATAACTGAC CAAGCTCCTT CATTAAT      5520

TATAGTTCCA GGGTCTCCAC AATATACAAT TATTGCTGAT GCAGGTGACT TTTATTT      5580

TCCTAGTTAT TACATGTTAC GAAAACGACG TAAACGTTTA CCATATTTTT TTTCAGA      5640

CTCTTTGGCT GCCTAGTGAG GCCACTGTCT ACTTGCCTCC TGTCCCAGTA TCTAAGG      5700

TAAGCACGGA TGAATATGTT GCACGCACAA ACATATATTA TCATGCAGGA ACATCCA      5760

TACTTGCAGT TGGACATCCC TATTTTCCTA TTAAAAAACC TAACAATAAC AAAATAT      5820

TTCCTAAAGT ATCAGGATTA CAATACAGGG TATTTAGAAT ACATTTACCT GACCCCA      5880

AGTTTGGTTT TCCTGACACC TCATTTTATA ATCCAGATAC ACAGCGGCTG GTTTGGG      5940

GTGTAGGTGT TGAGGTAGGT CGTGGTCAGC CATTAGGTGT GGGCATTAGT GGCCATC      6000

TATTAAATAA ATTGGATGAC ACAGAAAATG CTAGTGCTTA TGCAGCAAAT GCAGGTG      6060

ATAATAGAGA ATGTATATCT ATGGATTACA AACAAACACA ATTGTGTTTA ATTGGTT      6120

AACCACCTAT AGGGAACAC TGGGGCAAAG GATCCCCATG TACCAATGTT GCAGTAA      6180

CAGGTGATTG TCCACCATTA GAGTTAATAA ACACAGTTAT TCAGGATGGT GATATGG      6240

ATACTGGCTT TGGTGCTATG GACTTTACTA CATTACAGGC TAACAAAAGT GAAGTTC      6300

TGGATATTTG TACATCTATT TGCAAATATC CAGATTATAT TAAAATGGTG TCAGAAC      6360

ATGGCGACAG CTTATTTTTT TATTTACGAA GGGAACAAAT GTTTGTTAGA CATTTAT      6420

ATAGGGCTGG TACTGTTGGT GAAAATGTAC CAGACGATTT ATACATTAAA GGCTCTG      6480

CTACTGCAAA TTTAGCCAGT TCAAATTATT TTCCTACACC TAGTGGTTCT ATGGTTA      6540

CTGATGCCCA AATATTCAAT AAACCTTATT GGTTACAACG AGCACAGGGC CACAATA      6600

GCATTTGTTG GGGTAACCAA CTATTTGTTA CTGTTGTTGA TACTACACGC AGTACAA      6660

TGTCATTATG TGCTGCCATA TCTACTTCAG AAACTACATA TAAAAATACT AACTTTA      6720

AGTACCTACG ACATGGGGAG GAATATGATT TACAGTTTAT TTTTCAACTG TGCAAAA      6780

CCTTAACTGC AGACGTTATG ACATACATAC ATTCTATGAA TTCCACTATT TTGGAGG      6840

GGAATTTTGG TCTACAACCT CCCCCAGGAG GCACACTAGA AGATACTTAT AGGTTTG      6900

CCCAGGCAAT TGCTTGTCAA AAACATACAC CTCCAGCACC TAAAGAAGAT GATCCCC      6960
```

-continued

| | | |
|---|---|---|
| AAAAATACAC TTTTTGGGAA GTAAATTTAA AGGAAAAGTT TTCTGCAGAC CTAGATC | 7020 |
| TTCCTTTAGG ACGCAAATTT TTACTACAAG CAGGATTGAA GGCCAAACCA AAATTTA | 7080 |
| TAGGAAAACG AAAAGCTACA CCCACCACCT CATCTACCTC TACAACTGCT AAACGCA | 7140 |
| AACGTAAGCT GTAAGTATTG TATGTATGTT GAATTAGTGT TGTTTGTTGT GTATATG | 7200 |
| GTATGTGCTT GTATGTGCTT GTAAATATTA AGTTGTATGT GTGTTTGTAT GTATGGT | 7260 |
| ATAAACACGT GTGTATGTGT TTTTAAATGC TTGTGTAACT ATTGTGTCAT GCAACAT | 7320 |
| TAAACTTATT GTTTCAACAC CTACTAATTG TGTTGTGGTT ATTCATTGTA TATAAAC | 7380 |
| ATTTGCTACA TCCTGTTTTT GTTTTATATA TACTATATTT TGTAGCGCCA GGCCCAT | 7440 |
| GTAGCTTCAA CCGAATTCGG TTGCATGCTT TTTGGCACAA AATGTGTTTT TTTAAAT | 7500 |
| TCTATGTCAG CAACTATGGT TTAAACTTGT ACGTTTCCTG CTTGCCATGC GTGCCAA | 7560 |
| CCTGTTTTCC TGACCTGCAC TGCTTGCCAA CCATTCCATT GTTTTTTACA CTGCACT | 7620 |
| TGCAACTACT GAATCACTAT GTACATTGTG TCATATAAAA TAAATCACTA TGCGCCA | 7680 |
| CCTTACATAC CGCTGTTAGG CACATATTTT TGGCTTGTTT TAACTAACCT AATTGCA | 7740 |
| TTGGCATAAG GTTTAAACTT CTAAGGCCAA CTAAATGTCA CCCTAGTTCA TACATGA | 7800 |
| GTGTAAAGGT TAGTCATACA TTGTTCATTT GTAAAACTGC ACATGGGTGT GTGCAAA | 7860 |
| ATTTTGGGTT ACACATTTAC AAGCAACTTA TATAATAATA CTAA | 7904 |

(2) INFORMATION FOR SEQ ID NO: 2:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 2:

UAACUGUCAA AAGCC                                                        15

(2) INFORMATION FOR SEQ ID NO: 3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 3:

ACUGUGUCCU GAAGAA                                                 16

(2) INFORMATION FOR SEQ ID NO: 4:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 4:

GGCUUUUAGA AGUUA                                                       15

(2) INFORMATION FOR SEQ ID NO: 5:

(i) SEQUENCE CHARACTERISTICS:
    (A) LENGTH: 16 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 5:

```
UUCUUCAGAG AACAGU                                            16
```

(2) INFORMATION FOR SEQ ID NO: 6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 6:
```
GGCTTTTAGA AGTTA                                             15
```

(2) INFORMATION FOR SEQ ID NO: 7:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
TTCTTCAGAG AACAGT                                            16
```

(2) INFORMATION FOR SEQ ID NO: 8:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
UUCUUCAGAG AACAGUACCA GAGAAACACA CGGACUUCGG UCCGUGGUAU AUUACCUGG   60
A                                                                61
```

(2) INFORMATION FOR SEQ ID NO: 9:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
UUCUUCAGAG AACAGUACCA GAGCGUCACA CGGACUUCGG UCCGUGGUAU AUUACCUGG   60
A                                                                61
```

(2) INFORMATION FOR SEQ ID NO: 10:

(i) SEQUENCE CHARACTERISTICS:
    (A) LENGTH: 60 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 10:

GGCUUUUAGA AGUUAACCAG AGAAACACAC GGACUUCGGU CCGUGGUAUA UUACCUGGU    60

(2) INFORMATION FOR SEQ ID NO: 11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 11:

CAGCAATACA ACAAACCG                                                18

(2) INFORMATION FOR SEQ ID NO: 12:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 12:

CACGTAGAAA CCCAGC                                                  16

(2) INFORMATION FOR SEQ ID NO: 13:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 13:

TAGATTATGG TTTCTGAGAA CA                                           22

(2) INFORMATION FOR SEQ ID NO: 14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 14:

TGACGGGGTC ACCCACACTG TGCCCCATCT A                                 31

(2) INFORMATION FOR SEQ ID NO: 15:

(i) SEQUENCE CHARACTERISTICS:
        (A) LENGTH: 31 base pairs
        (B) TYPE: nucleic acid
        (C) STRANDEDNESS: single

```
            (D) TOPOLOGY: linear (ii) MOLECULE TYPE: cDNA (xi) SEQUENCE DESCRIPTION: SEQ ID NO: 15:

CTAAGAAGCA TTTGCGGTGG ACGATGGAGG G                              31

(2) INFORMATION FOR SEQ ID NO: 16:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 16:

UUCUUCAGAG AACAGUGGCU UUUGACAGUU A                              31

(2) INFORMATION FOR SEQ ID NO: 17:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO: 17:

TCTTCAGAG AACAGTGGCT TTTGACAGTT A                               31
```